United States Patent
Avellanet

(12) 
(10) Patent No.: US 6,278,057 B1
(45) Date of Patent: *Aug. 21, 2001

(54) MEDICAL DEVICES INCORPORATING AT LEAST ONE ELEMENT MADE FROM A PLURALITY OF TWISTED AND DRAWN WIRES AT LEAST ONE OF THE WIRES BEING A NICKEL-TITANIUM ALLOY WIRE

(75) Inventor: Francisco J. Avellanet, Coral Gables, FL (US)

(73) Assignee: General Science and Technology Corp., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/143,751

(22) Filed: Aug. 31, 1998

Related U.S. Application Data

(63) Continuation-in-part of application No. 09/060,969, filed on Apr. 15, 1998, now Pat. No. 6,137,060, and a continuation-in-part of application No. 09/087,476, filed on May 29, 1998, and a continuation-in-part of application No. 09/044,203, filed on Mar. 17, 1998, and a continuation-in-part of application No. 08/843,405, filed on May 2, 1997, now Pat. No. 5,994,647, and a continuation-in-part of application No. 08/963,686, filed on Nov. 4, 1997, now Pat. No. 6,049,042, and a continuation-in-part of application No. PCT/US97/18057, filed on Oct. 7, 1997.

(51) Int. Cl.$^7$ .............................. H01B 11/06; H01B 5/08
(52) U.S. Cl. ...................... 174/36; 174/126.1; 174/128.1
(58) Field of Search ............................ 174/126.1, 128.1, 174/94 R, 90, 128.2, 36; 606/106, 107, 108, 129

(56) References Cited

U.S. PATENT DOCUMENTS

| | | | | |
|---|---|---|---|---|
| 3,131,469 | * | 5/1964 | Glaze .................................. | 29/470.5 |
| 3,620,212 | | 11/1971 | Fannon, Jr. ........................ | 128/130 |
| 4,027,677 | | 6/1977 | Schulman et al. .................. | 128/418 |
| 4,037,324 | | 7/1977 | Andreasen ............................ | 32/14 |
| 4,215,703 | * | 8/1980 | Willson .............................. | 128/772 |
| 4,233,690 | | 11/1980 | Akins ................................... | 3/1.5 |
| 4,493,320 | | 1/1985 | Treat .............................. | 128/303.15 |
| 4,830,003 | | 5/1989 | Wolff ................................. | 128/343 |
| 4,830,262 | * | 5/1989 | Ishibe ................................. | 228/156 |
| 4,925,445 | * | 5/1990 | Sakamoto et al. ................. | 604/95 |
| 5,112,136 | | 5/1992 | Sakuma et al. ...................... | 374/44 |
| 5,146,928 | | 9/1992 | Esser .................................. | 128/756 |
| 5,201,323 | | 4/1993 | Vermeulen ......................... | 128/756 |
| 5,201,741 | | 4/1993 | Dulebohn ........................... | 606/113 |
| 5,213,111 | * | 5/1993 | Cook et al. ........................ | 128/772 |
| 5,230,348 | * | 7/1993 | Ishibe et al. ...................... | 128/772 |
| 5,263,964 | | 11/1993 | Purdy ................................ | 606/200 |
| 5,322,508 | * | 6/1994 | Viera .................................. | 604/52 |
| 5,376,100 | | 12/1994 | Lefebvre ............................ | 606/180 |
| 5,423,829 | | 6/1995 | Pham et al. ...................... | 606/108 |
| 5,429,139 | * | 7/1995 | Sauter ............................... | 128/772 |
| 5,439,000 | * | 8/1995 | Gunderson et al. .............. | 128/664 |
| 5,520,194 | * | 5/1996 | Miyata et al. ..................... | 128/772 |
| 5,597,378 | * | 1/1997 | Jervis ................................ | 606/78 |
| 5,601,600 | | 2/1997 | Ton ................................... | 606/206 |
| 5,639,277 | | 6/1997 | Mariant et al. .................... | 606/191 |
| 5,667,525 | | 9/1997 | Ishibashi ........................... | 606/206 |

FOREIGN PATENT DOCUMENTS

| | | | |
|---|---|---|---|
| 0197692 | * | 5/1922 | (DE) . |
| 0480427 A1 | * | 10/1991 | (EP) . |
| 0649636 A2 | * | 8/1994 | (EP) . |
| 197692 | * | 5/1923 | (GB) . |

\* cited by examiner

*Primary Examiner*—Dean A. Reichard
*Assistant Examiner*—William H. Mayo, III
(74) *Attorney, Agent, or Firm*—David P Gordon; David S Jacobson; Thomas A Gallagher

(57) ABSTRACT

Medical devices are provided which utilize a highly flexible cable of two and preferably three or more strands of wire, at least one of which is a nickel-titanium alloy strand. The strands are twined to form a wire rope which is drawn through successive dies to reduce its diameter until the outer surface of the cable is substantially smooth. A cable of all nickel-titanium alloy strands has been found to have an improved elasticity over a superelastic nickel-titanium wire of the same diameter. The cable is used in medical devices in which increased elasticity of a wire-like element is desired. Twisted and drawn cables incorporating a strand of a radiopaque metal or alloy with one or more nickel-titanium strands may be used in devices in which radiopacity of a flexible portion of the device is desired. Twisted and drawn cables incorporating a strand of a highly electrically conductive metal or alloy with one or more nickel-titanium strands may be used in devices in which electrical conductivity of a flexible portion of the device is desired.

27 Claims, No Drawings

MEDICAL DEVICES INCORPORATING AT LEAST ONE ELEMENT MADE FROM A PLURALITY OF TWISTED AND DRAWN WIRES AT LEAST ONE OF THE WIRES BEING A NICKEL-TITANIUM ALLOY WIRE

This application is a continuation-in-part of U.S. Ser. No. 09/060,969 filed Apr. 15, 1998 now U.S. Pat. No. 6,137,060, a continuation-in-part of U.S. Ser. No. 09/087,476 filed on May 29, 1998, a continuation-in-part of U.S. Ser. No. 09/044,203 filed on Mar. 17, 1998, a continuation-in-part of U.S. Ser. No. 08/843,405 filed May 2, 1997 now U.S. Pat. No. 5,994,647, a continuation-in-part of U.S. Ser. No. 08/963,686 filed Nov. 4, 1997 now U.S. Pat. No. 6,049,042, and a continuation-in-part of PCT/US97/18057 filed Oct. 7, 1997 which claimed priority from U.S. Pat. No. 6,019,736 and U.S. Ser. Nos. 08/730,489 filed Oct. 11, 1996 and Ser. No. 08/554,336 filed Nov. 6, 1995, both now abandoned, all of which are hereby incorporated by reference herein in their entireties.

BACKGROUND OF THE INVENTION

1. Field of the Invention

This invention relates broadly to medical devices incorporating elements having a low modulus of elasticity. More particularly, this invention relates to medical devices incorporating one or more cable elements made from a plurality of twisted and drawn wires, at least one of the wires comprising a nickel-titanium alloy.

2. State of the Art

Wires are utilized throughout the medical arts. In many medical devices a particularly desirable feature for the wires is high elasticity. For example, in baskets and snares high elasticity may be the most important property of the wires used. The elasticity of the wires comprising snares and baskets is a factor in the extent to which each may be compressed for insertion to the surgical site and yet still be able to expand upon use. In addition, higher elasticity permits the baskets and snares to be contracted about smaller radii.

The need for highly flexible self-expanding stents is also well-known. Flexibility not only permits proper stent deployment, but also enables the stent to better conform to the vascular walls.

In endoscopic instruments, a control wire is often coupled between a proximal handle and a distal end effector. The control wire is used to translate movement of the handle into operation of the end effector. The wire must be able to easily bend through the tortuous paths through which endoscopic instruments are guided.

Wire flexibility is also important in numerous other medical devices. For that reason, the medical arts have recently had much interest in nickel-titanium alloy (Nitinol) wires which exhibit superelastic characteristics. For the same reasons which have made Nitinol so popular, an even more elastic wire than a nickel-titanium wire is desirable for many medical device applications.

In addition, with respect to many medical devices, the art has gone to great lengths and expense to provide radiopaque materials to the distal end of Nitinol elements (see, e.g., U.S. Pat. No. 5,520,194 to Miyata et al.). This is particularly required in devices using very fine (i.e., small diameter) Nitinol wires which cannot easily be seen during fluoroscopy. However, radiopaque materials are difficult to attach to the Nitinol components owing, in part, to their dissimilarity with the Nitinol material. Moreover, it is preferable in certain applications to have a highly elastic component which conducts electricity sufficiently to permit cautery functions or to permit the component to function as an electrical lead. However, nickel-titanium alloys are not particularly good conductors.

SUMMARY OF THE INVENTION

It is therefore an object of the invention to provide a variety of medical devices which utilize one or more nickel-titanium alloy cables that exhibit improved flexibility characteristics over nickel-titanium alloy wires of the art.

It is another object of the invention to provide medical devices with a radiopaque highly elastic element.

It is also object of the invention to provide medical devices which include a conductive highly elastic element.

It is a further object of the invention to provide medical devices which include a radiopaque, conductive, and highly elastic element.

In accord with these objects, which will be discussed in detail below, medical devices are provided which utilize a highly flexible cable of two and preferably three or more strands of wire, at least one of which is a nickel-titanium alloy strand, which are twined to form a wire rope which is drawn through successive dies to reduce its diameter until the outer surface of the cable is substantially smooth. A cable of all nickel-titanium alloy strands has been found to have an improved elasticity over a nickel-titanium wire of the same diameter. The cable is used in medical devices in which increased elasticity of a wire-like element is desired. Twisted and drawn cables incorporating one or more nickel-titanium strands and at least one strand of a radiopaque metal or alloy may be used in devices in which radiopacity of an elastic portion of the device is desired. Twisted and drawn cables incorporating one or more nickel-titanium alloys strands and at least one strand of a highly electrically conductive metal or alloy may be used in devices in which electrical conductivity of an elastic portion of the device is desired. Twisted and drawn cables incorporating at least one strand of nickel-titanium alloy with at least one strand of a radiopaque metal or alloy with at least one strand of a highly electrically conductive alloy may be used in devices in which radiopacity of an electrically conductive elastic portion of a device is desired.

Additional objects and advantages of the invention will become apparent to those skilled in the art upon reference to the detailed description.

DETAILED DESCRIPTION OF THE PREFERRED EMBODIMENTS

The invention will be described by first introducing the concept of cables formed from multistrand twisted and drawn wires. Then, with respect to multistrand twisted and drawn cables formed from nickel-titanium (Nitinol) wire, the benefit of such cables over nickel-titanium wires of the same diameter will be discussed. Finally, examples will be provided illustrating how such cables can be substituted for conventional wires, and particularly nickel-titanium alloy wires, in medical devices to achieve the beneficial results of the invention.

The invention is the improvement of a variety of medical devices by utilizing therein a cable of two and preferably three or more strands of wire, at least one of which is a nickel-titanium wire, which are twined to form a wire rope. The wire rope is drawn through successive dies to reduce its diameter until the outer surface of the cable is substantially smooth, the cross section of the cable is substantially circular, and the overall diameter of the wire rope is reduced by 20–50%. The cable is then annealed to remove the effects of cold working.

When the cable is constructed from only nickel-titanium alloy wires, the resulting cable has been found to have an improved flexibility (i.e., a lower modulus of elasticity) relative to a single nickel-titanium wire of the same diameter as the cable. In order to exemplify the benefit of a twisted and drawn cable comprised of nickel-titanium strands, three strands of 0.010 inch diameter Nitinol wire were helically twisted at a lay length of approximately 0.080 inches to form a wire rope of approximately 0.021" diameter, and fed through successive dies of 0.019", 0.018", 0.016", 0.014", and 0.013" diameters to form a Nitinol cable. After each die, it was noticed that the Nitinol cable rebounded to a slightly larger diameter than the diameter of the die. Thus, after the last die, the Nitinol cable was found to have a diameter of 0.014" rather than 0.013". The so-formed Nitinol cable was then annealed for approximately one minute at a temperature of approximately 500° C. to remove the effects of cold-working from the cable. Pieces of the resulting twisted and drawn Nitinol cable were then subjected to bend radius testing by wrapping pieces of the cables around pins of different diameters and by clamping the cable back on itself with a pair of pliers to simulate a zero-diameter bend. Comparison tests were conducted on 0.014" diameter Nitinol wires (single strands). The results of the bend radius testing are set forth in Table 1, with percent recovery calculated according to $(180°-x°)/180°$, where x° is the angle of set taken by the wire or cable from longitudinal axis of the wire before the bend:

TABLE 1

| Pin Diameter (inch) | % Recovery NiTi cable | % Recovery NiTi Wire |
|---|---|---|
| .201 | 100 | 100 |
| .169 | 100 | 98.3 |
| .155 | 100 | 98.0 |
| .139 | 100 | 94.4 |
| .121 | 99.1 | 93.8 |
| .093 | 98.8 | 92.7 |
| .078 | 98.0 | 91.6 |
| .039 | 96.1 | 63.8 |
| .034 | 91.6 | 55.5 |
| .027 | 95.8 | 53.6 |
| 0 diameter bend | 38.8 | 6.6 |

From the results of the tests set forth in Table 1, it will be appreciated that the Nitinol cable of the invention exhibited significantly increased flexibility relative to the same diameter Nitinol wire. For example, the Nitinol cable appears to be able to be twisted around a pin having a diameter of as little as approximately nine times the diameter of the cable without taking a set (i.e., with substantially 100% recovery), while the Nitinol wire takes a set when twisted around a pin having a diameter of approximately twelve or thirteen times the diameter of the wire. Furthermore, the Nitinol cable recovers over 90% when twisted around a pin having a diameter of only approximately two times the diameter of the cable, while the Nitinol wire will bend approximately ninety degrees when similarly twisted. Thus, it will be appreciated that the recoverable elastic strain of the Nitinol cable is significantly lower than the recoverable elastic strain of the Nitinol wire. Furthermore, it is believed that the Nitinol cable of the invention exhibits highly elastic characteristics prior to entering the stress-induced martensite (SIM) phase, which occurs with Nitinol wires. Moreover, twisted and drawn Nitinol cables exhibit shape memory characteristics consistent with Nitinol wires, and may be similarly trained to form desired shapes. In addition, such cables have high torqueability and can exhibit strong radial force. Similar improvements have been recorded with cables of other diameters.

In addition, one or more strands of a radiopaque material, e.g., gold, silver, or platinum-iridium, may be twisted and drawn with at least one nickel-titanium alloy strand. The resulting cable is highly elastic and is radiopaque. In accord with the invention, the cable so formed may be used in devices in which radiopacity of a flexible portion of a medical device is desired, e.g., for viewing the flexible portion during fluoroscopic procedures.

Also, one or more highly electrically conductive strands, e.g., platinum, gold, silver, copper, or aluminum, may be twisted and drawn with one or more nickel-titanium strands to form a cable having desirable elastic properties and good electrical conductance. In accord with the invention, the cable so formed may be used in devices in which high electrical conductivity of a flexible portion of a medical device is desired.

Moreover, in accord with the invention, cables incorporating at least one strand of a nickel-titanium alloy, at least one strand of a radiopaque metal or alloy, and at least one strand of an electrically conductive metal may be used in devices in which a radiopaque, conductive, and flexible portion of a device is desired. It will be appreciated that the radiopaque strand and strand having high conductance may be the same strand, e.g., a gold or silver strand.

Particular cables, their manufacture, and their properties are described in detail in co-pending U.S. application Ser. Nos. 08/856,571 to Avellanet et al., Ser. No. 08/843,405 and Ser. No. 08/963,686 to Avellanet, Ser. No. 09/044,203 and Ser. No. 09/087,476 to Avellanet et al., Ser. No. 09/048,746 to Bales et al., and Ser. No. 09/060,969 to Avellanet, which are all hereby incorporated by reference herein in their entireties. From reference to the respective disclosures, it will be appreciated that any particular cable composition described herein may be made by one skilled in the art. Following are examples of uses of twisted and drawn cables in medical devices.

EXAMPLE 1

Surgical Baskets

Baskets are typically used to remove calculi in the form of kidney stones, gallstones and the like from the body without requiring major surgery. Baskets are generally formed from wires defining at least two loops relatively oriented to form a cage-like enclosure. U.S. Pat. No. 5,064,428 to Cope et al. discloses a basket device using a plurality of superelastic wires to form a basket at the distal end of the device, and is hereby incorporated by reference herein in its entirety. U.S. Pat. No. 5,496,330 to Bates et al., which is also hereby incorporated by reference herein in its entirety, discloses another device having a basket comprised of a relatively larger number of shape memory wires for increasing the contact between the basket and entrapped calculi. However, it is noted by Bates et al. that increasing the number of wires requires the use of wires with relatively smaller diameters. Such smaller diameter wires are weaker and limit the radially acting dilating force that the wires exert against surrounding tissue when the retrieval basket expands, thus making it more difficult to entrap calculi. Furthermore, such baskets are difficult to cannulate through the gallbladder anatomy. Baskets are required to pass smoothly through such areas as the cystic ducts, the common bile duct, and the intestines, as well as being able to retrieve stones from distal sites while causing minimal injury and discomfort to the patient.

By using multistrand twisted and drawn highly elastic cables incorporating at least one Nitinol wire to form the basket device, a number of disadvantages in the prior art are overcome. First, baskets comprised of highly elastic twisted and drawn cables can be more easily maneuvered through the tortuous pathways of the anatomical systems in which they are used, as the cable loops forming the basket can be more tightly compressed. Second, the cables are more torqueable and can be better steered. Third, smaller diameter cables can be used which have comparable strength to relatively larger wires and which can exert the requisite radial force to maneuver surrounding tissue to facilitate capture and removal of the calculi. Fourth, by using a radiopaque twisted and drawn cable, the baskets can more easily and inexpensively be made radiopaque for fluoroscopic viewing during surgical procedures.

It will be further appreciated that in a basket construction, not all of the 'wires' need by twisted and drawn multifilament cables. In fact, by utilizing the twisted and drawn cables in conjunction with more conventional wires, the basket may be provided with portions of relatively higher and lower radial strengths, thereby aiding steerability. Similarly, a combination of cables, and preferably also wires, of varying diameters can also provide an increased level of flexibility in a desired direction.

It will also be understood that a basket made of conventional materials may be provided on a shaft comprised of a multifilament twisted and drawn cable incorporating at least one Nitinol wire. The shaft is joined to the basket at the distal end of the shaft via a sleeve by welding, soldering, or crimping. This arrangement provides higher torqueability than provided with existing instruments.

EXAMPLE 2

Snares

Snares are used for the endoscopic removal of tissue growths within a body cavity. An exemplar snare device is described in U.S. Pat. No. 5,201,741 to Dulebohn, which is hereby incorporated by reference herein in its entirety. Snare devices generally include an elongate tubular member and an elastic wire (e.g., Nitinol) forming a loop movable distally and proximally within the tubular member to cause the loop to change size. The wire is moved relatively distally to the tubular member to enlarge the loop to surround the tissue, and then relatively proximally to constrict the loop about the growth to excise the growth. The wire may be trained to naturally assume the desired enlarged size. However, a concern with snares is the ability to constrict the loop without plastically deforming the wire about a small radius which would destroy the functionality of the snare.

As described above with respect to Table 1, a twisted and drawn Nitinol cable exhibits significantly increased flexibility relative to the same diameter Nitinol wire and will bend about a relatively smaller diameter before plastically deforming. Thus, the twisted and drawn Nitinol cable has a higher recoverable elastic strain than a Nitinol wire of the same diameter and permits the snare loop to be constricted about a relatively tighter radius than a Nitinol wire. In addition, the twisted and drawn cable has high torqueability and can be better steered around the tissue to be excised.

In addition, it is known to construct snare devices having bipolar cautery capability. See, for example, U.S. Pat. No. 4,493,320 to Treat, which is hereby incorporated by reference herein in its entirety. Such snare devices include an electrically insulated tubular member having two lumina, a pair of flexible electrically conductive snare wires extending from the lumina, an electrically insulating connector for mechanically uniting but electrically insulating the snare wires in a form of a surgical loop extending from one end of the tubular member, and an attachment for electrically connecting the opposite ends of the snare wires to a cautery current source. It will be appreciated that conductive twisted and drawn elastic cables incorporating one or more Nitinol wires may be used in such a device in place of the known conductive wires to enhance the elasticity of the snare.

EXAMPLE 3

Control Cables for Endoscopic and Laparoscopic Instruments

Endoscopic instruments typically include a proximal actuation handle, a tubular member, one or two control wires, and a distal end effector. The distal end effector may be any of numerous types. For example, U.S. Pat. No. 5,507,296 to Bales et al. discloses a biopsy forceps jaw assembly; U.S. Pat. No. 5,667,525 to Ishibashi discloses a grasping forceps; U.S. Pat. No. 5,395,386 to Slater discloses scissors end effectors; and U.S. Pat. No. 5,549,606 to McBrayer et al. discloses a bipolar grasper end effector. Each of the aforementioned patents is hereby incorporated by reference herein in its entirety for their disclosure of the particular end effector described therein, for the operation of endoscopic instruments in general, and for any other disclosure useful to one skilled in the art. It will be appreciated that other end effectors may alternatively be provided.

The tubular member of the endoscopic instrument, which is often a coil, preferably includes a distally positioned clevis means on which the end effectors are rotatably coupled. The control wire (or wires) extends through the tubular member. The actuation handle includes a stationary member, coupled to the proximal end of either the control wire (or wires) or the tubular member, and a movable member coupled to the proximal end of the other of the control wire (or wires) and the tubular member, such that moving the movable member relative to the stationary member imparts movement of the control wire (or wires) relative to the tubular member to operate the end effector.

The control wire is generally a stainless steel wire. However, as the control wire must be able to easily bend through the tortuous paths through which the endoscopic instrument is guided, control wire flexibility is important. Therefore, in accord with the invention, an elastic twisted and drawn cable incorporating at least one Nitinol wire, as described above, is used as the control 'wire'.

In addition, U.S. Pat. No. 5,482,054 to Bales, which is hereby incorporated herein in its entirety, discloses a bipolar biopsy forceps. The control wires of the disclosed device may be electrically conductive and elastic twisted and drawn cables, as described above, such that bipolar cautery capability is provided via the control 'cables'.

Similarly, laparoscopic instruments may be provided with one or more control cables in the same manner as the above described endoscopic instruments.

EXAMPLE 4

Rotary Atherectomy (Thrombectomy) Device

U.S. Pat. No. 5,376,100 to Lefebvre, which is hereby incorporated by reference herein in its entirety, discloses an atherectomy or thrombectomy device which comprises a rotary member having flexible filiform elements joined at their distal and proximal ends. When the rotary member is rotated at high speed, the elements are transversely expanded by the effect of the centrifugal force.

The flexible filiform elements and the rotary member may both be comprised of elastic twisted and drawn cable, preferably comprising a plurality of nickel-titanium wires. It will be appreciated that such twisted and drawn cable has excellent flexibility, and is well-adapted for the filiform elements. It will be further appreciated that the cable has high torqueability, and is well-adapted for the rotary member.

EXAMPLE 5

Stents

Self-expanding stents are generally formed from a spring metal or other resilient material and are deployable through a guiding catheter on a delivery catheter covered with a lubricous sleeve. When the sleeve is withdrawn over the self-expanding stent, the stent automatically expands so as to exert pressure against the surrounding vessel wall. Self-expanding stents are disclosed in, e.g., U.S. Pat. No. 4,580,568 to Gianturco; U.S. Pat. No. 4,830,003 to Wolff et al.; U.S. Pat. No. 5,549,635 to Solar; U.S. Pat. No. 5,562,697 to Christiansen; and U.S. Pat. No. 5,292,331 and U.S. Pat. No. 5,674,278 to Boneau, which are all hereby incorporated by reference herein in their entireties. Such stents are typically formed from a single small diameter wire having a multiplicity of back and forth bends in a zig-zag or sinusoidal path to form an elongate self-expanding structure, or a plurality of self-expanding segments coupled by links, each of the segments defined by a wire having a zig-zag or sinusoidal path, or a plurality of plaited wires.

Self-expanding stents need to be flexible. Such flexibility determines the ease of which the stents may be maneuvered through the curves of blood vessels to the lesion site. In accord with the invention, a stent device is comprised of one or more nickel-titanium twisted and drawn cables. The enhanced flexibility of a stent device thus comprised facilitates insertion of the stent device to its deployment location. Also, in accord with the invention, stent devices may be made from a twisted and drawn elastic cable incorporating both a Nitinol wire and a radiopaque wire. The radiopaque wire in the cable enables improved fluoroscopic viewing of the stent device within the human body to ensure that the device is properly positioned and further ensure that the device is functioning properly.

EXAMPLE 6

Resection Electrodes

Electrosurgical resection is a procedure in which damaged or enlarged tissue is excised with an electrocautery probe. U.S. Pat. No. 5,569,244 to Hahnen discloses an electrocautery probe, and is hereby incorporated by reference herein in its entirety. The electrocautery probe has a distal resection electrode which is mounted between a pair of arms. The arms are joined at their proximal ends to an electrode lead which is coupled via a handle to a source of cautery current. The electrodes are generally made from cobalt chromium or carbonless stainless steel.

The resection procedure involves applying a cauterizing voltage to the electrode and moving the electrode slowly through or over a tissue. Thermal energy is applied through the electrode, and the tissue in contact is excised. The resectoscope and cautery probe are also useful in procedures for resecting the prostate, endometrium, uterus, ureter, or renal pelvis.

The resection electrodes of the art are replaced with resection electrodes comprised of a multistrand twisted and drawn cable. The strands comprising the cable preferably include strands of nickel-chromium, platinum-iridium, or tungsten, in addition to strands of nickel-titanium. The cable may be trained according to methods well-known in the art, to take various shapes, e.g., curved and angular, which facilitate cutting through and cautery of the tissue being resected.

EXAMPLE 7

Embolization Coils

Metallic microcoils are used to bridge (embolize) aneurysms in cerebral arteries. The procedure for deploying the coil involves the use of a microcatheter which is delivered through the vasculature to the site of the aneurysm. When the catheter is in place, a stainless steel wire with a platinum coil soldered or otherwise coupled to its distal end is fed through the catheter to the site of the aneurysm. The coil is separated from the wire by the application of a small current which causes the solder to melt, or by mechanical means. Embolization coils are described in U.S. Pat. No. 5,263,964 to Purdy, U.S. Pat. No. 5,639,277 to Mariant et al., U.S. Pat. No. 5,601,600 to Ton, U.S. Pat. No. 5,423,829 to Pham et al., and U.S. Pat. No. 5,122,136 to Guglielmi et al., which are all hereby incorporated by reference herein in their entireties.

According to the invention, the delivery wire and/or the coil is comprised of nickel-titanium multifilament twisted and drawn cable. Preferably, the cable comprising the coil includes at least one strand of platinum or other radiopaque material.

EXAMPLE 8

Myocardial Leads

The use of myocardial leads is well known, in either bipolar or monopolar configurations, to stimulate the surface of a heart by the application of electrical pulses is well known. U.S. Pat. No. 4,027,677 to Schulman, which is hereby incorporated by reference herein in its entirety, discloses the art of pacer leads in general. Typically, a myocardial lead consists of an electrode having a pin extending therefrom. The pin is inserted and secured in the myocardium and electrical pulses are supplied to the electrode from an appropriate source, such as a pacemaker, via a wire connected between the electrode and the pacemaker. The electrode is generally in the form of a bent platinum rod, one end of which serves as the electrode pin. Platinum, while biocompatible and able to pass electrical currents either anodically or cathodically into a saline solution, such as the solution present in the body, without corrosion, tends to break quite easily under the stress of heart motion and body movement.

The improved electrode of the invention comprises a twisted and drawn multifilament cable including nickel-titanium strands and one or more highly electrically conductive strands. Preferably the conductive strand (or strands) is made from platinum. The nickel-titanium strands may be surrounded by the platinum strands to inhibit corrosion, or, as nickel-titanium is not particularly corrosive, the nickel-titanium strands may surround the platinum strands.

Alternatively, the strands of nickel-titanium and platinum may be intertwined. The resulting cable is able to pass current, resist corrosion, and is highly elastic relative to pure platinum wires.

EXAMPLE 9

Orthodontic Cables

U.S. Pat. No. 4,037,324 to Andreasen, the disclosure of which is hereby incorporated by reference herein in its entirety, discloses the use of dental wires made of nickel-titanium alloys instead of conventional 18-8 stainless steel wires. The Andreasen reference discloses the advantage of using wires which have a lower elastic modulus and higher elastic limit than stainless steel. In accord with the invention, multifilament twisted and drawn cables made from nickel-titanium strands provide an orthodontic cable having a lower elastic modulus and higher elastic limit than nickel-titanium orthodontic wires.

EXAMPLE 10

Heart Valves

U.S. Pat. No. 4,233,690 to Akins, the disclosure of which is hereby incorporated by reference herein in its entirety, discloses the use of a conventional shape memory alloy ring to hold a sewing cuff to the body of an artificial heart valve. The ring is replaced with a twisted and drawn nickel-titanium cable such that it has greater elasticity than the ring of the prior art.

EXAMPLE 11

IUDs

U.S. Pat. No. 3,620,212 to Fannon et al., the disclosure of which is hereby incorporated by reference herein in its entirety, discloses an intrauterine contraceptive device (IUD) proposed to be formed from a shape memory alloy. In accord with the invention, the IUD is formed from a twisted and drawn nickel-titanium alloy cable.

EXAMPLE 12

Cytology Brushes

In some cases, obtaining a forceps biopsy may be difficult. In these cases, the practitioner may obtain cellular samples by brushing with a cytology brush. The cytology brush generally comprises an elongate shaft for extension through an endoscope and a plurality of typically helically arranged bristles at the distal end of the shaft. Exemplar cytology brushes are described in U.S. Pat. No. 5,146,928 to Esser and U.S. Pat. No. 5,201,323 to Vermeulen, which are hereby incorporated by reference herein in their entireties. In accord with the invention, either or both of the bristles of the brush and the shaft may be comprised of nickel-titanium twisted and drawn cable. Bristles of a nickel-titanium cable structure are more flexible than the presently-provided bristles, and a nickel-titanium cable shaft is more torqueable than present shafts.

There have been described and illustrated herein a number of medical devices which are improved by utilizing one or more twisted and drawn cable elements in place of elements otherwise constructed. While particular devices and embodiments of the invention have been described (with reference to U.S. Patents incorporated herein), it is not intended that the devices be limited to the embodiments disclosed in the incorporated references, only that such references provide the broad teaching of the respective devices. Particularly, each device in the incorporating reference should be read as a representative for all devices of the type of such device and the scope of the invention should be interpreted in this light. In addition, it is clear that other medical devices can be provided which utilize the superelastic cable of the invention. For example, papillotomy knives, surgical staples, braiding elements in catheters, braiding elements for tubes for blood pumps and peristaltic pumps, and other medical devices may incorporate the described cable in accord with the contemplated scope of the invention. Moreover, it will be appreciated that the invention may be utilized in both reusable and disposable instruments. It will therefore be appreciated by those skilled in the art that yet other medical devices could provided with the twisted and drawn cable without deviating from the spirit and scope of the invention as so claimed.

What is claimed is:

1. In a medical device for temporary or permanent insertion or implantation into a human body, the improvement comprising:

at least one element comprising at least two wires first twisted and and then drawn through at least one die to form a flexible cable, at least one of said at least two wires being a nickel-titanium alloy wire.

2. The improvement according to claim 1, wherein:

said at least two twisted wires comprises at least three nickel-titanium alloy wires.

3. The improvement according to claim 1, wherein:

said at least two twisted wires includes at least one wire having a radiopacity greater than said nickel-titanium alloy wire.

4. The improvement according to claim 1, wherein:

said at least two twisted wires includes at least one wire made from a conductive material having greater conductance than said a t least one nickel-titanium alloy wire.

5. The improvement according to claim 4, wherein:

said conductive material is comprised of at least one of platinum, gold, silver, copper, and aluminum.

6. The improvement according to claim 1, wherein:

said at least two twisted wires includes at least three twisted wires, namely at least one wire made from a radiopaque material and at least one wire made from a conductive material having greater conductance than each of said radiopaque material and nickel-titanium alloy.

7. The improvement according to claim 1, wherein:

said medical device is an endoscopic instrument.

8. The improvement according to claim 7, wherein:

said at least one element is a control cable in said endoscopic instrument.

9. The improvement according to claim 1, wherein:

said medical device is a surgical basket device having a basket, and said at least one element is a component of said basket.

10. The improvement according to claim 1, wherein:

said medical device is a surgical snare device, and said at least one element comprises a snare.

11. The improvement according to claim 10, wherein:

said snare is a bipolar snare.

12. The improvement according to claim 1, wherein:

said medical device is a rotary atherectomy device.

13. The improvement according to claim 12, wherein:
said at least one element comprises a rotary member.

14. The improvement according to claim 12, wherein:
said at least one element comprises a plurality of filiform elements.

15. The improvement according to claim 1, wherein:
said medical device is a self-expanding stent.

16. The improvement according to claim 1, wherein:
said medical device is an electrocautery probe.

17. The improvement according to claim 16, wherein:
said at least one element is an electrode of said electrocautery probe.

18. The improvement according to claim 1, wherein:
said medical device is an embolization coil.

19. The improvement according to claim 1, wherein:
said medical device is a myocardial lead.

20. The improvement according to claim 19, wherein:
said at least one element is an electrode of said myocardial lead.

21. The improvement according to claim 1, wherein:
said medical device is an orthodontic cable.

22. The improvement according to claim 1, wherein:
said medical device is a heart valve.

23. The improvement according to claim 22, wherein:
said at least one element is a ring component of said heart valve.

24. The improvement according to claim 1, wherein:
said medical device is an IUD.

25. The improvement according to claim 1, wherein:
said medical device is a cytology brush.

26. The improvement according to claim 25, wherein:
said at least one element is a plurality of bristles of said cytology brush.

27. The improvement according to claim 25, wherein:
said at least one element is a shaft of said cytology brush.

* * * * *